United States Patent
Hanieh (10) Patent No.: US 10,709,696 B1
(45) Date of Patent: *Jul. 14, 2020

(54) THERAPEUTIC AGENTS FOR TREATING DISEASES ASSOCIATED WITH CHRONIC INFLAMMATION AND SCREENING METHOD

(71) Applicant: KING FAISAL UNIVERSITY, Hofouf (SA)

(72) Inventor: Hamza Naim Ahmad Hanieh, Aqaba (JO)

(73) Assignee: King Faisal University, Hofouf (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,727

(22) Filed: Dec. 17, 2019

Related U.S. Application Data (63) Continuation of application No. 16/396,719, filed on Apr. 28, 2019, now Pat. No. 10,512,639.

(51) Int. Cl.
*A61K 31/4439* (2006.01)
*G01N 33/50* (2006.01)

(52) U.S. Cl.
CPC ....... *A61K 31/4439* (2013.01); *G01N 33/502* (2013.01)

(58) Field of Classification Search
CPC ................................ A61K 31/4439
See application file for complete search history.

(56) References Cited

U.S. PATENT DOCUMENTS 10,512,639 B1 * 12/2019 Hanieh ............... G01N 33/502
2018/0016576 A1   1/2018 Kishimoto et al.
2018/0195064 A1   6/2018 Kishimoto et al.

FOREIGN PATENT DOCUMENTS

JP              6069075 A        4/1985

OTHER PUBLICATIONS

Khan et al., Synthesis and biological activity of some isoniazid based 1,3,4-oxadiazole derivatives, Indian Journal of Chemistry, vol. 43B, Jun. 2004, pp. 1302-1305.*
Kumar, B., et al., "Latest Update on Pharmacological Activities of 1,3,4-Oxadiazole Derivatives," J. Cell Sci. Ther., 7:1, (2016).
Hanieh, H., et al., "Arid5a Stabilizes OX40 mRNA in murine CD4+ T cells by recognizing a stem-loop structure in its 3'UTR," Eur. J. Immunol., 48(4): pp. 593-604, (2018).
Masuda, K., "Arid5a regulates naive CD4+ T cell fate through selective stabilization of Stat3 mRNA," JEM, 213(4): pp. 605-619 (2016).
Masuda, K., "Arid5a controls IL-6 mRNA stability, which contributes to elevation of IL-6 level in vivo," PNAS, 110(23) pp. 9409-9414 (2013).
Zaman, M. M. et al., "Arid5a exacerbates IFN-γ-mediated septic shock by stabilizing T-bet mRNA," PNAS, 113(41) pp. 11543-11548 (2016).

* cited by examiner

*Primary Examiner* — Svetlana M Ivanova
(74) *Attorney, Agent, or Firm* — Richard C. Litman; Nath, Goldberg & Meyer

(57) ABSTRACT

A method for treating autoimmune diseases or a disease associated with chronic inflammation can include administering to a subject in need thereof a therapeutically effective amount of a pharmaceutical composition comprising an Arid5a inhibitor and a pharmaceutically acceptable carrier. The Arid5a inhibitor can have the formula

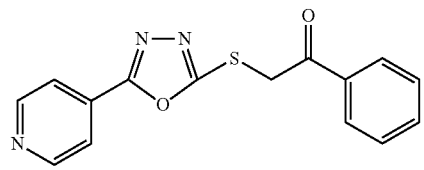

or a pharmaceutically acceptable salt thereof. The disease associate with chronic inflammation can be multiple sclerosis. A screening method can include identifying candidate Arid5a inhibitors through in silico predicted binding to Arid5a target domains and confirming Arid5a inhibition through in vitro binding assays.

3 Claims, 7 Drawing Sheets

THERAPEUTIC AGENTS FOR TREATING DISEASES ASSOCIATED WITH CHRONIC INFLAMMATION AND SCREENING METHOD

CROSS-REFERENCE TO RELATED APPLICATIONS

This application is a continuation of application Ser. No. 16/396,719, filed Apr. 28, 2019, now pending.

INCORPORATION BY REFERENCE OF MATERIAL SUBMITTED IN COMPUTER READABLE FORM

The Applicants hereby incorporate by reference the sequence listing contained in the ASCII text file titled 32087_15_sequence_listing_ST25.txt, created Dec. 5, 2018 and having 1.23 KB of data.

BACKGROUND

1. Field

The disclosure of the present patent application relates to RNA-binding (RBP) inhibitors, and particularly, to Arid5a inhibitors, methods of screening for Arid5a inhibitors, and methods of treating chronic inflammation and diseases associated with chronic inflammation, such as multiple sclerosis, using an Arid5a inhibitor.

2. Description of the Related Art

Multiple sclerosis (MS) is a widespread neurological autoimmune disease that includes episodes of demyelination in the central nervous system (CNS) resulting in different levels of disabilities. MS is the most prevalent non-traumatic cause of CNS complications in young people worldwide. MS patients present variable patterns of symptoms, including relapsing remittance characterized by intermittent exacerbations. These exacerbations usually include inflammatory attacks associated with neurological symptoms and impairment of vision and memory.

The pathogenesis of MS involves both the innate and adaptive immune responses. Innate immune cells, such as macrophages, contribute to pathogenesis of MS by secretion of pro-inflammatory cytokines such as interleukin-6 (IL-6) and tumor necrosis factor-$\alpha$ (TNF-$\alpha$). In addition, the antigen-presenting cells (APCs) of the innate immune response provide cytokine milieus that direct differentiation of naïve CD4$^+$ T cells into effector cells. These differentiated cells, mainly IL-17-secreting T helper 17 (Th17) cells are implicated in MS pathogenesis. Therefore, reducing any or all of the above mentioned pro-inflammatory cytokines, which are greatly implicated in autoimmune inflammation, has been an area of active investigation to develop a therapeutic strategy to treat MS.

Common treatments for MS typically focus on reducing exacerbations and disease progression rather than offering a cure. These treatments are classified as disease-modifying treatments (DMT). For example, interferon-$\beta$ (IFN-$\beta$) has been used as an efficient DMT. However, this treatment is associated with increased levels of liver enzymes and flu-like symptoms. Other therapeutic agents such as mitoxantrone and humanized antibodies including daclizumab, natalizumab and alemtuzumab exert promising therapeutic effects in MS patients. However, recent studies have shown that such treatments have severe side effects. Mitoxantrone is associated with cardiotoxicity and acute leukemia, alemtuzumab is associated with autoimmune-associated complications, and natalizumab is associated with progressive multifocal leukoencephalopathy.

Thus, alternative therapeutic agents for treating diseases associated with chronic inflammation and screening methods for agents solving the aforementioned problems are desired.

SUMMARY

A method for treating chronic inflammation or a disease associated with chronic inflammation can include administering to a subject in need thereof a therapeutically effective amount of a pharmaceutical composition comprising an AT-rich interactive domain-containing 5a (Arid5a) inhibitor and a pharmaceutically acceptable carrier. The diseases associated with chronic inflammation can include autoimmune diseases. The autoimmune diseases can include, for example, multiple sclerosis. The Arid5a inhibitor can inhibit the RNA-binding activities of Arid5a and the subsequent stabilizing functions on target mRNAs encoding pro-inflammatory mediators. The Arid5a inhibitor can include 1-Phenyl-2-(5-pyridin-4-yl-[1,3,4]oxadiazol-2-ylsulfanyl)-ethanone (herein, "POE"), having a chemical structure according to the general formula:

or a pharmaceutically acceptable salt thereof. It should be understood that the dihedral angles shown for POE are shown for illustrations purposes only, and the Arid5a inhibitor POE includes derivatives of POE having any dihedral angles.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

As used herein, a "subject" includes mammals, e.g., humans, dogs, cats, sheep, cows, rats, mice, and the like.

As used herein, "Arid5a" refers to AT-rich interactive domain-containing 5a (Arid5A), a protein that stabilizes mRNAs encoding pro-inflammatory mediators, including signal transducer and activator of transcription 3 (Stat3), IL-6, and OX40 (CD134).

According to an embodiment, a method for treating chronic inflammation or diseases associated with chronic inflammation can include administering to a subject in need thereof a therapeutically effective amount of a pharmaceutical composition comprising an Arid5a inhibitor and a pharmaceutically acceptable carrier. The diseases associated with chronic inflammation can include autoimmune diseases. The autoimmune diseases can include, for example, multiple sclerosis. The Arid5a inhibitor, also referred to herein as "therapeutic agent," can inhibit the RNA-binding activities of Arid5a and the subsequent stabilizing functions on target mRNAs encoding pro-inflammatory mediators. The Arid5a inhibitor can include 1-phenyl-2-(5-pyridin-tl[1,3,4]oxadiazol-2-ylsulfanyl)-ethanone (herein, "POE"), having a chemical structure according to the general formula:

(Formula 1)

or a pharmaceutically acceptable salt thereof. It should be understood that the dihedral angles shown for POE are shown for illustrations purposes only, and the Arid5a inhibitor POE includes derivatives of POE having any dihedral angles.

Arid5a is required for pathogenesis of experimental autoimmune encephalomyelitis (EAE), a murine model of MS, by stabilizing the mRNAs of Il6 and OX40. Arid5a is also required for differentiation and effector functions of Th17 cells by stabilizing Stat3 mRNA. Accordingly, the Arid5a inhibitor can be an anti-inflammatory agent.

An embodiment of the present subject matter is directed to a pharmaceutical composition comprising the Arid5a inhibitor compound and a pharmaceutically acceptable carrier.

An embodiment of the present subject matter is directed to a method of making the pharmaceutical composition including mixing the Arid5a inhibitor with a pharmaceutically acceptable carrier. For example, the method of making the pharmaceutical composition can include mixing the Arid5a inhibitor under sterile conditions with a pharmaceutically acceptable carrier and preservatives, buffers, or propellants to create the pharmaceutical composition; and presenting the pharmaceutical composition in a form suitable for daily, weekly, monthly, or life-long administration.

In an embodiment, the composition of the present subject matter may be administered orally, nasally, rectally, parenterally, intracisternally, intra vaginally, intraperitoneally, topically, transdermally, by surgical implantation, or by intravenous or intramuscular injections. In an embodiment, the composition of the present subject matter is administered in a form selected from liquid oral preparations, solid oral preparations, parenteral preparations, injectable suspensions, and liposomes.

The Arid5a inhibitor or pharmaceutical compositions can be administered to a subject by any suitable route. For example, the compositions can be administered orally (including bucally and sublingually), nasally, rectally, intracisternally, intra vaginally, intraperitoneally, topically, transdermally (as by powders, ointments, or drops), parenterally, and/or by surgical implantation. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding the composition in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

To prepare the pharmaceutical composition, the Arid5a inhibitor or a salt thereof, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

For parenteral use, the carrier will usually comprise sterile water, though other ingredients, for example, for purposes such as aiding solubility or for preservation, may be included. Injectable suspensions may also be prepared, in which case appropriate liquid carriers, suspending agents, and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The Arid5a inhibitor of the present disclosure also can be administered in the form of liposomes. Liposomes generally are derived from phospholipids or other lipid substances and are formed by mono- or multi-lamellar hydrated liquid crystals dispersed in an aqueous medium. Any nontoxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

The present compositions can include adjuvants such as preservatives, wetting agents, emulsifying agents, and dispersing agents. Prevention of the action of microorganisms can be ensured by the inclusion of various anti-bacterial and anti-fungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, monthly, or life-long administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the Arid5a inhibitor or an amount effective to treat an autoimmune disease, such as multiple sclerosis, may be determined initially from the Examples described herein and adjusted for specific desired Arid5a inhibitor using routine methods.

In an embodiment, the present subject matter includes a method of identifying candidate Arid5a inhibitors. An in silico analysis may be conducted to screen for candidate inhibitors. For example, molecular docking simulations can be used for screening a candidate inhibitor useful for treating autoimmune diseases, such as multiple sclerosis. Candidate Arid5a inhibitors may be selected based on predicted interactions with a target domain in Arid5a. The target domain may be Pocket X, a feature of the Arid5a protein including, but not limited to, amino acids Glu53, Phe56, Leu57, Val58, Leu84, Tyr88, Leu133, Val134, Tyr137, Val138, His140, and Leu141. Candidate Arid5a inhibitors are then tested in vitro by examining the candidate inhibitors' effects on the stabilizing function of Arid5a on target mRNA encoding proinflammatory mediators using a luciferase assay, PCR, and ELISA tests. The mRNAs can be of OX40, Il6, and Stat3. Candidate Arid5a inhibitors are then tested in vitro by examining the candidate inhibitors' effects on Arid5a binding activities to stem loops in the 3'UTR of target mRNAs using a RNA-protein binding system. Finally, the therapeutic potential of candidate Arid5a inhibitors may be assessed in vivo using a model of an autoimmune disease, such as $MOG_{35-55}$-induced experimental multiple sclerosis. A therapeutic potential can be determined according to clinical scores, cytokine levels, and OX40 expression.

The following examples illustrate the present teachings.

Example 1

Experimental Conditions

Experiments described herein were conducted using the following general experimental conditions.

Female C57BL/6 mice (6-8 weeks) were purchased originally from Charles River and maintained under specific pathogen-free conditions. All in vivo and in vitro animal experiments were performed using these mice at Laboratory of Physiology and Immunology, King Faisal University, Saudi Arabia, in accordance with institutional guidelines.

The peritoneal macrophages were stimulated in vitro with 0.5 µg/mL lipopolysaccharides (LPS) (Sigma-Aldrich) for 24 h. The $CD4^+CD62L^+$ T cells were isolated and purified from spleen using the MACS isolation kit (Miltenyi). The T cells were cultured in the presence of anti-CD3/CD8 dynabeads (Invitrogen), recombinant mouse IL-6 (30 ng/mL; R&D Systems), recombinant transforming growth factor-β (TGF-β) (4 ng/mL; R&D Systems), anti-interferon-γ (IFN-γ) and anti-IL-4 (10 µg/mL; Biolegend) for 72 h to generate Th17 cells.

The cytokines and mRNA were quantified as follows. A first strand of cDNA was synthesized from total RNA by using the TaqMan reverse transcription kit. The cDNA was amplified in the real-time PCR system ViiA7 using TaqMan gene expression assays of OX40 (Mm01261022_m1), Stat3 (Mm01219775_m1) and the endogenous control Gapdh (Mm99999915_g1). Kits, probes and reagents were from Applied Biosystems. The relative expression of mRNAs was calculated by ΔΔCt method. For cytokines quantification in serum and cell culture supernatants, ELISA kits of IL-17a, IL-6, TNF-α (Invitrogen) were used following the manufacturer's instructions.

Flow cytometry analysis was conducted using polarized Th17 cells or CNS-derived CD4$^+$ T cells, which were fixed and stained with Per-CP-Cy5.5-conjugated anti-CD4 antibodies and PE-conjugated anti-OX40 antibodies (Biolegend). Analysis was carried out using Flowsight (Amnis).

Data are presented as mean±SD from representative experiment studied in triplicates out of at least three independent experiments produced similar results. The statistical significance between means was tested by one-way ANOVA. Two-way ANOVA was used to analyze the statistical significance of the data obtained from EAE clinical score (*=p<0.05).

Example 2

Luciferase Assay of POE Inhibitor Effects on Arid5a Functions

The potential interaction between Arid5a inhibitor POE and Arid5a was predicted by in silico modeling. The effect of the potential interaction on the stabilizing function of Arid5a on the 3'UTR of target mRNAs was tested using a luciferase assay.

Figure 1A:
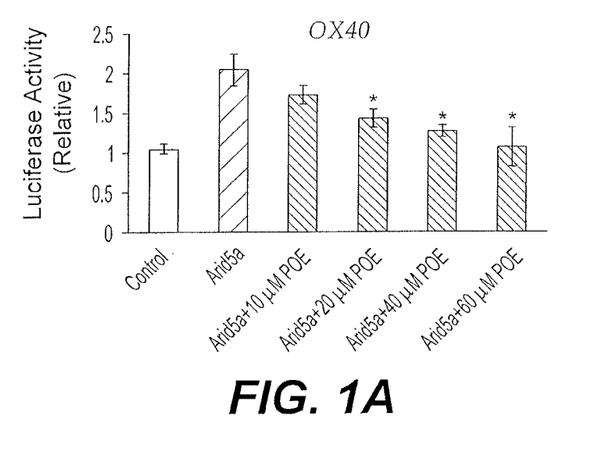
FIG. 1A depicts a graph of the effects of POE on Arid5a-mediated stability of the OX40 3'UTR.
Figure 1B:
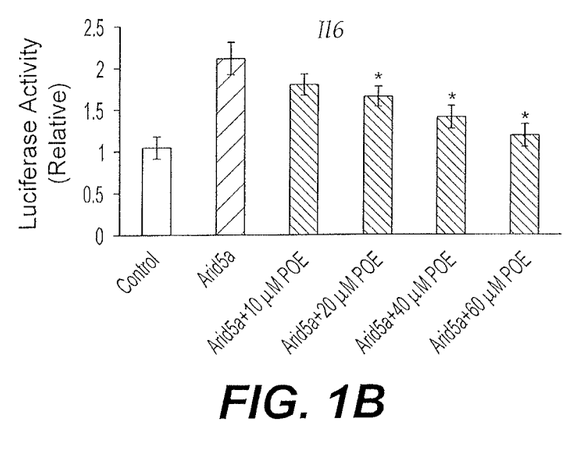
FIG. 1B depicts a graph of the effects of POE on Arid5a-mediated stability of the Il6 3'UTR.
Figure 1C:
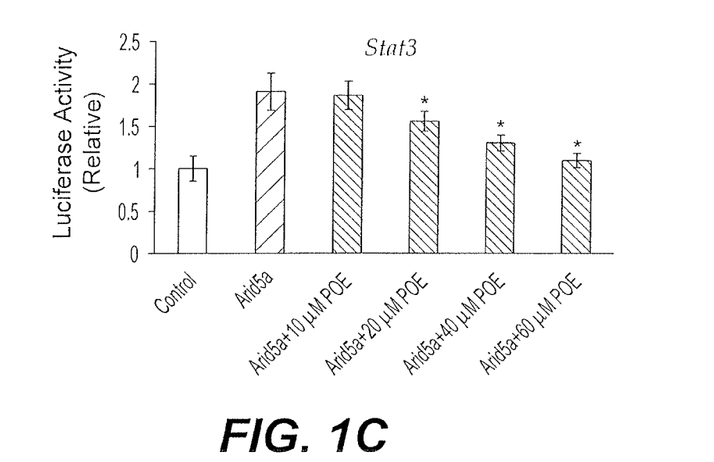
FIG. 1C depicts a graph of the effects of POE on Arid5a-mediated stability of the Stat3 3'UTR.

Briefly, HEK293T cells were transfected with luciferase pGL-3 and empty pcDNA3.1 plasmids (Control), or pGL-3 plasmid encoding the 3'UTR of OX40, Il6 or Stat3, together with Arid5a-expressing pcDNA3.1 plasmid. The cells were treated with DMSO (Control and Arid5a) or POE (10-60 μM) dissolved in DMSO. The mouse Arid5a (NP_0011-65676.1) cDNA (WT; ENSMUST00000115032.7) was cloned in a Flag-tagged pcDNA3.1 plasmid at Xba1 and Ecor1. Renila-expressing plasmid was used as a control. Luciferase activity from cell lysates is shown relative to Control in FIGS. 1A-1C. The graphs depicted in FIGS. 1A-1C demonstrate that the Arid5a inhibitor POE inhibits Arid5a stabilizing function on the 3'UTR of OX40, Il6, and Stat3 mRNAs in a dose-dependent manner.

Example 3

Luciferase Assay of POE Inhibitory Effects on Pocket X-Mutant Arid5a

The Arid5a inhibitor POE was further predicted by in silico modeling to interact with Arid5a, specifically through Pocket X, a feature of the Arid5a protein including but not limited to amino acids Glu53, Phe56, Leu57, Val58, Leu84, Tyr88, Leu133, Val134, Tyr137, Val138, His140, and Leu141. The primary sequence of Arid5a (NP_0011-65676.1) was acquired from Ensemble and the 590 amino acid variant ENSMUST00000115032.7 was selected. The 3D coordinate of Arid5a was built to include residues 50-149 (SEQ ID NO: 1) of Arid5a. The binding sites of the target protein were identified using Q-site Finder and Pocket finder, and the binding domain (Pocket X) was chosen based on highest druggability score. Molecular docking simulation was carried out using SYBYLX 2.1 software (Tripos Associates Inc.). The candidate inhibitors were sorted based on predicted binding energy (CHEMPLP).

The effect of the interaction between POE with specific residues in Pocket X on the stabilizing function of Arid5a on the 3'UTR of target mRNAs was confirmed by using a luciferase assay.

Briefly, HEK293T cells were transfected with luciferase pGL-3 and empty pcDNA3.1 plasmids (Control), or pGL-3 plasmid encoding the 3'UTR of OX40, Il6 or Stat3, together with Arid5a-expressing pcDNA3.1 plasmid. Substitution mutations were introduced to the wild-type (WT) Arid5a at Phe56, Leu84, Val134 and Tyr137. Single point mutations were used to substitute Phe56 (TTC) with Cys (TGC) and Val134 (GTC) with Ala (GCC). Sequential point mutations were used to substitute Leu84 (CTG) with Ala (GCG) and Tyr137 (TAT) with Ala (GCT). Luciferase activity from cell lysates is shown relative to Control in FIGS. 2A-2C.

Figure 2A:
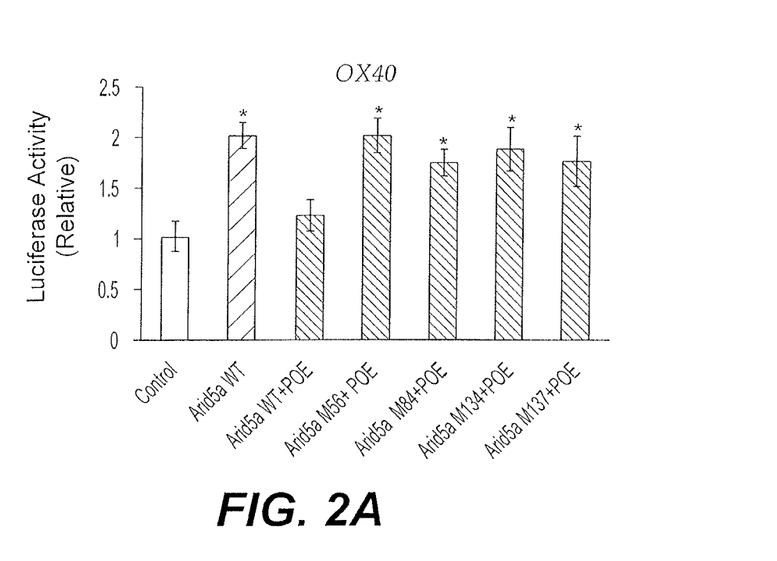
FIG. 2A depicts a graph of the effect of substitution mutations in Arid5a on POE-mediated inhibition of Arid5a stabilizing function on the OX40 3'UTR.
Figure 2B:
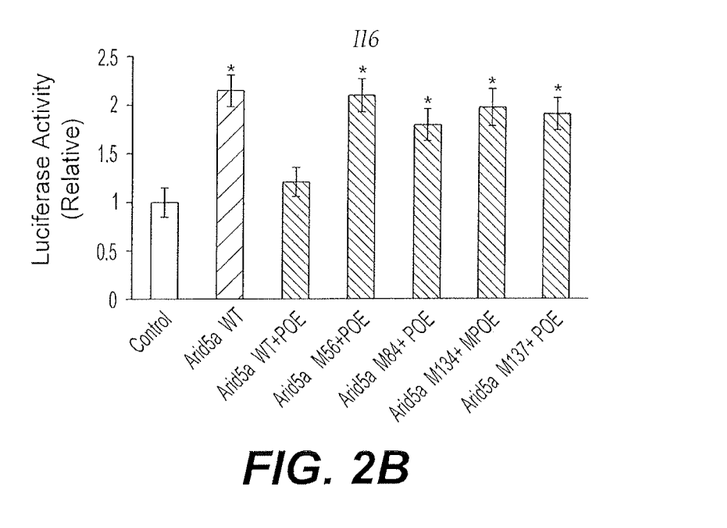
FIG. 2B depicts a graph of the effect of substitution mutations in Arid5a on POE-mediated inhibition of Arid5a stabilizing function on the Il6 3'UTR.
Figure 2C:
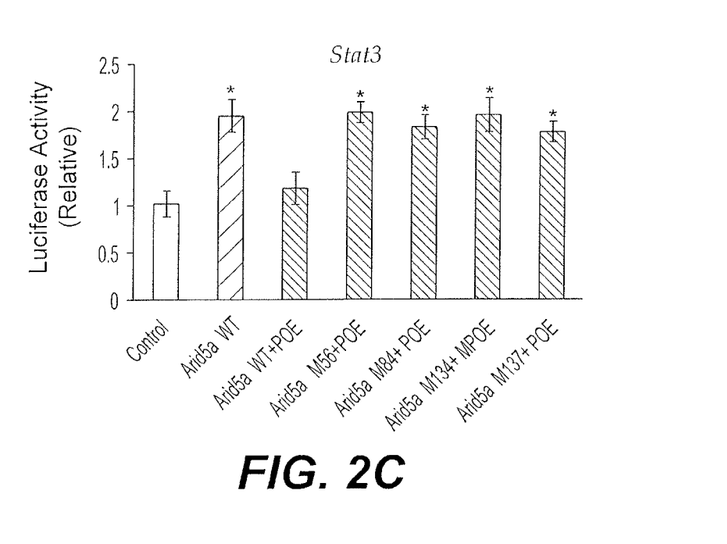
FIG. 2C depicts a graph of the effect of substitution mutations in Arid5a on POE-mediated inhibition of Arid5a stabilizing function on the Stat3 3'UTR.

As shown in FIG. 2A, substitution mutations at Phe56, Leu84, Val134 and Tyr137 of Pocket X abolish the inhibitory effects of POE (40 μM) on the stabilizing function of Arid5a on OX40 3'UTR. As shown in FIG. 2B, substitution mutations at Phe56, Leu84, Val134 and Tyr137 of Pocket X abolish the inhibitory effects of POE (40 μM) on the stabilizing function of Arid5a on Il6 3'UTR. As shown in FIG. 2C, substitution mutations at Phe56, Leu84, Val134 and Tyr137 of Pocket X abolish the inhibitory effects of POE (40 μM) on the stabilizing function of Arid5a on Stat3 3'UTR.

Example 4

Anti-Inflammatory Activity of POE

Figure 3A:
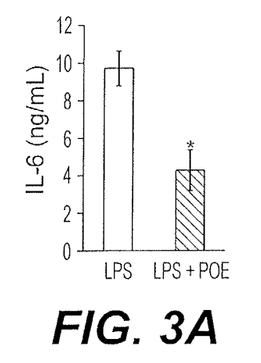
FIG. 3A depicts a graph of the effects of POE on IL-6 production by macrophages.
Figure 3B:
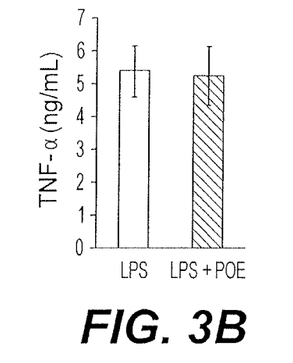
FIG. 3B depicts a graph of the effects of POE on TNF-$\alpha$ production by macrophages.
Figures 3C, 3D:
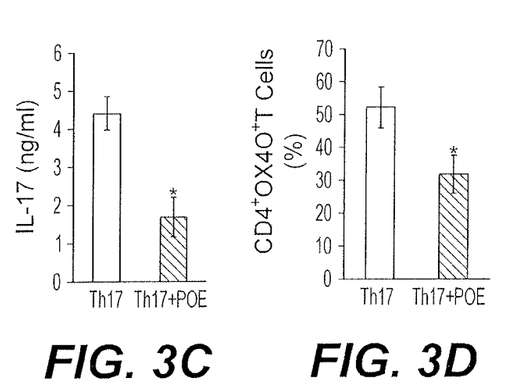
FIG. 3C depicts a graph of the effects of POE on IL-17 production by differentiated Th17 cells.
FIG. 3D depicts a graph of the effects of POE on CD4 OX40+ T cells in differentiated Th17 cells.

The anti-inflammatory activity of the Arid5a inhibitor POE was tested in vitro by measuring secretion of pro-inflammatory cytokines by macrophages and polarized Th17 cells. Briefly, peritoneal macrophages were stimulated with LPS (0.5 μg/mL) for 24 h in presence or absence of POE (40 μM). Naïve (CD4$^+$CD62L$^+$) T cells from the spleen were differentiated under Th17-polarizing conditions for 72 h in presence or absence of POE (40 μM). Levels of IL-6 and TNF-α were quantified in supernatant of macrophage culture; the results are shown in FIGS. 3A and 3B. IL-17 was quantified in supernatant of polarized Th17 cell culture; the results are shown in FIG. 3C. The percentage of CD4$^+$/OX40$^+$ T cells in the polarized Th17 cells was determined using flow cytometry; the results are shown in FIG. 3D. Stat3 mRNA expression in the polarized Th17 cells was quantified by real-time PCR and normalized to Gapdh mRNA; the results are shown relative to those of untreated Th17 cells in FIG. 3E.

Figure 3E:
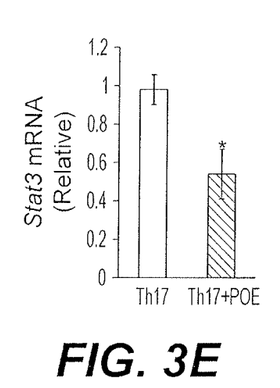
FIG. 3E depicts a graph of the effect of POE on Stat3 mRNA expression in differentiated Th17 cells.

As shown in FIG. 3A, POE reduces the level of IL-6 in cell culture supernatant of LPS-stimulated macrophages compared to LPS alone. As shown in FIG. 3B, POE does not affect the level of TNF-α in cell culture supernatant of LPS-stimulated macrophages compared to LPS alone. As shown in FIG. 3C, POE reduces the level of IL-17 in cell culture supernatant of polarized Th17 cells compared to untreated Th17 cells. As shown in FIG. 3D, POE reduces the frequency of CD4$^+$/OX40$^+$ T cells in polarized Th17 cells compared to untreated Th17 cells. As shown in FIG. 3E, POE reduces the expression of Stat3 mRNA in polarized Th17 cells compared to untreated Th17 cells.

Example 5

RNA-Arid5a Binding Assay

Figure 4:
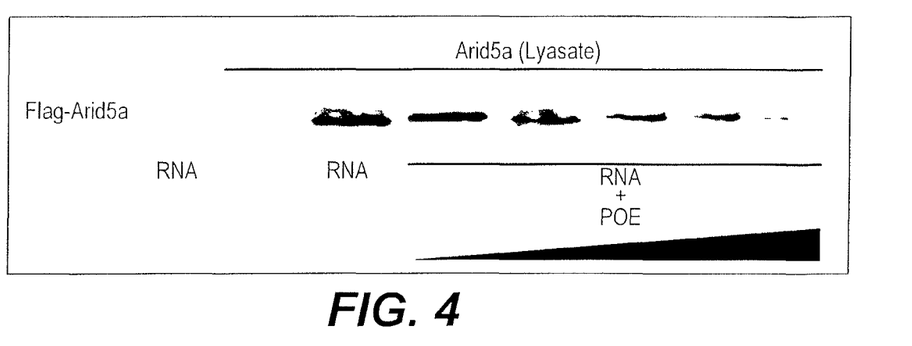
FIG. 4 depicts the effect of POE on Arid5a binding to the alternative decay element (ADE)-like stem loop in the OX40 3'UTR.

An RNA-protein binding assay was performed to confirm that POE inhibits the physical binding of Arid5a to the (ADE)-like stem loop in the OX40 3'UTR. Briefly, a 3'-biotinylated OX40 ADE-like stem loop (RNA; 5'-UCCACACCGUUCUAGGUGCUGG-3') (SEQ ID NO: 2) was conjugated to streptavidin beads. The OX40 ADE-like stem loop/streptavidin bead conjugate was then mixed with Flag-Arid5a-enriched HEK293T cell lysate, washed, and proteins bound to RNA were eluted for immunoblot. Anti-Flag antibodies were used to detect Flag-Arid5a in the eluate by SDS-PAGE analysis. As shown in FIG. 4, POE inhibited the physical binding of Arid5a to OX40 ADE-like stem loop in a concentration-dependent manner.

Example 6

Therapeutic Effects of POE in Experimental Multiple Sclerosis

Briefly, EAE was induced in C57BL/6 female mice using $MOG_{35-55}$ (200 μg) emulsified in complete Freund's adjuvant containing 10 mg/mL heat-killed *Mycobacterium tuberculosis* H37Ra. Mice received two intraperitoneal injections of pertussis toxin (500 ng) on days 0 and 2. The mice received one intraperitoneal injection of POE (0.5 mg) or corn oil per day starting from day 0 for four consecutive days. Serum levels of IL-6 and TNF-α were quantified on day 24. Encephalitogenic CD4$^+$ T cells were isolated from lymph nodes of EAE mice and re-stimulated with $MOG_{35-55}$ (30 μg/mL) and IL-23 (23 ng/mL) for 72 h; thereafter IL-7 was quantified in cell culture supernatant by ELISA. OX40 mRNA and protein were quantified in CD4$^+$ T cells isolated from the CNS of EAE mice 10 days after disease induction. The mRNA was quantified by real-time PCR, normalized to Gapdh mRNA and presented relative to that of corn oil-treated EAE mice. The percentage of CD4$^+$/OX40$^+$ T cells was analyzed using flow cytometry.

Figure 5A:
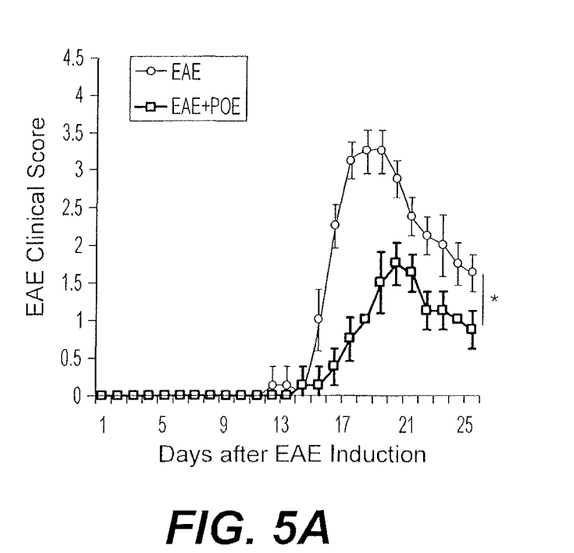
FIG. 5A depicts a graph of EAE score over time with and without POE treatment.
Figure 5B:
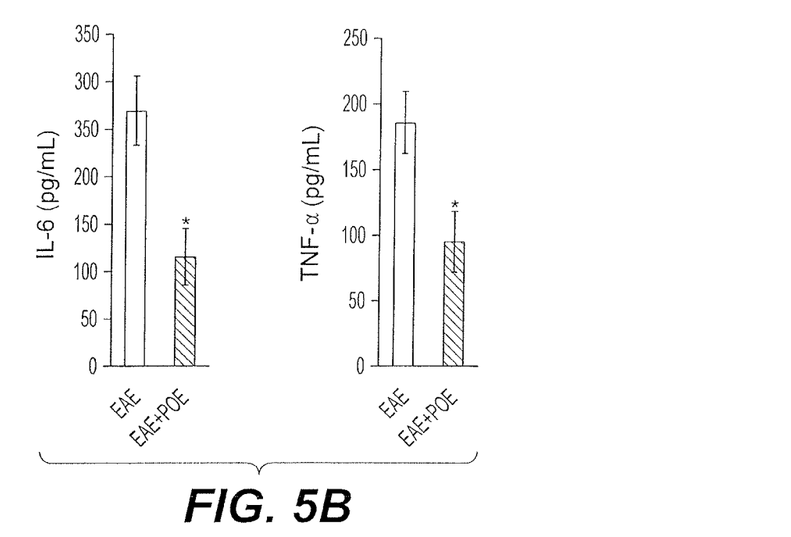
FIG. 5B depicts a graph of IL-6 and TNF-α serum levels in the EAE model with and without treatment with POE.
Figure 5C:
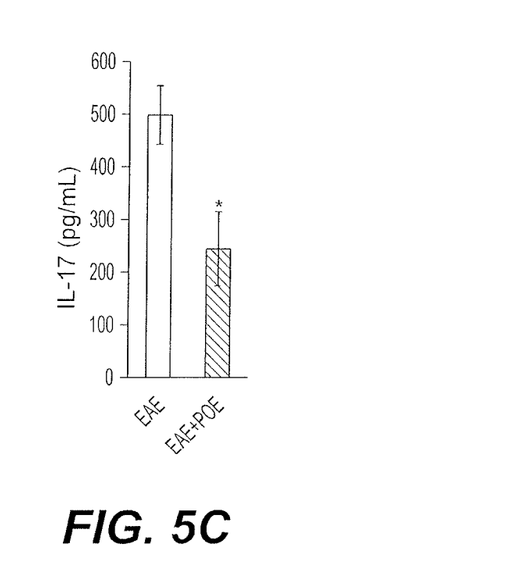
FIG. 5C depicts a graph of IL-17 production by encephalitogenic CD4+ T cells in response to restimulation in the EAE model with and without treatment with POE.
Figure 5D:
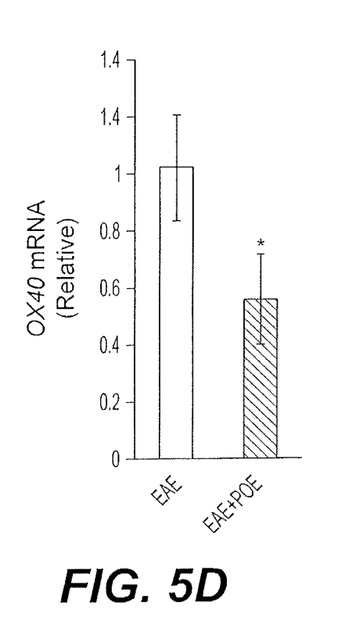
FIG. 5D depicts a graph of OX40 mRNA levels in CD4+ T cells isolated from the CNS in the EAE model with and without treatment with POE.
Figure 5E:
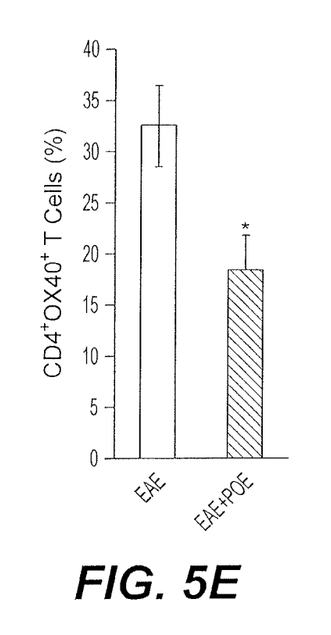
FIG. 5E depicts a graph of percentage of CD4+$^{OX}$40+ T cells isolated from the CNS in EAE model with and without treatment with POE.

As shown in FIG. 5A, POE treatment reduces EAE clinical scores compared to corn oil-treated mice (EAE). As shown in FIG. 5B, POE reduces serum levels of IL-6 and TNF-α compared to corn oil-treated mice (EAE). As shown in FIG. 5C, POE reduces the level of IL-17 in culture supernatant of encephalitogenic CD4$^+$ T cells in response to restimulation compared to corn oil-treated mice (EAE). As shown in FIG. 5D, POE reduces the expression of OX40 mRNA in CD4$^+$ T cells isolated from the CNS of EAE mice. As shown in FIG. 5E, POE reduces the frequency of CD4$^+$/OX40$^+$ T cells in the CNS of EAE mice.

It is to be understood that the therapeutic agents for treating diseases associated with chronic inflammation, screening method for the therapeutic agents, and method for treating diseases associated chronic inflammation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating multiple sclerosis, comprising: administering to a subject in need thereof an effective amount of an Arid5a inhibitor, wherein the Arid5a inhibitor comprises a compound having the formula or a pharmaceutically acceptable salt thereof, wherein the Arid5a inhibitor interacts with a target domain of Arid5a.

2. The method of treating multiple sclerosis according to claim 1, wherein the target domain is selected from the group consisting of amino acids Glu53, Phe56, Leu57, Val58, Leu84, Tyr88, Leu133, Val134, Tyr137, Val138, His140, and Leu141.

3. The method of treating multiple sclerosis according to claim 1, wherein the Arid5a inhibitor has a stabilizing function on one or more pro-inflammatory mediators selected from the group consisting of Il6 3'UTR, OX40 3'UTR, and Stat3 3'UTR.

* * * * *